US012758598B2

(12) United States Patent
Sato et al.

(10) Patent No.: US 12,758,598 B2
(45) Date of Patent: Oct. 13, 2026

(54) COMPOSITION FOR IMPROVING INFLAMMATION OF BRAIN TISSUE

(71) Applicant: MEIJI CO., LTD., Tokyo (JP)

(72) Inventors: Asako Sato, Tokyo (JP); Takayuki Toshimitsu, Tokyo (JP)

(73) Assignee: MEIJI CO., LTD., Tokyo (JP)

( * ) Notice: Subject to any disclaimer, the term of this patent is extended or adjusted under 35 U.S.C. 154(b) by 461 days.

(21) Appl. No.: 18/267,687

(22) PCT Filed: Dec. 13, 2021

(86) PCT No.: PCT/JP2021/045752
§ 371 (c)(1),
(2) Date: Jun. 15, 2023

(87) PCT Pub. No.: WO2022/131192
PCT Pub. Date: Jun. 23, 2022

(65) Prior Publication Data

US 2024/0058398 A1 Feb. 22, 2024

(30) Foreign Application Priority Data

Dec. 16, 2020 (JP) ................................ 2020-208555

(51) Int. Cl.
*A61K 35/747* (2015.01)
*A61K 35/00* (2006.01)
*A61P 29/00* (2006.01)

(52) U.S. Cl.
CPC ............ *A61K 35/747* (2013.01); *A61P 29/00* (2018.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 2015/0306158 | A1 | 10/2015 | Kim et al. | |
| 2018/0355445 | A1 | 12/2018 | Kim et al. | |
| 2022/0040243 | A1 | 2/2022 | Choi et al. | |
| 2023/0293605 | A1* | 9/2023 | Toshimitsu | A61K 35/20 424/93.45 |
| 2024/0058398 | A1 | 2/2024 | Sato et al. | |

FOREIGN PATENT DOCUMENTS

| | | | | |
|---|---|---|---|---|
| CA | 3 081 210 | | 5/2019 | |
| CN | 109153967 | | 1/2019 | |
| CN | 110066753 | | 7/2019 | |
| CN | 111110705 | | 5/2020 | |
| CN | 111202754 | | 5/2020 | |
| CN | 111394276 | | 7/2020 | |
| CN | 111655839 | | 9/2020 | |
| CN | 111728111 | | 10/2020 | |
| CN | 112204129 | | 1/2021 | |
| CN | 112386614 | | 2/2021 | |
| EP | 3 747 988 | | 12/2020 | |
| JP | 2015-526085 | | 9/2015 | |
| JP | 2015-213501 | | 12/2015 | |
| JP | 2018-531595 | | 11/2018 | |
| JP | 2019-527713 | | 10/2019 | |
| JP | 2020-515240 | | 5/2020 | |
| JP | 2021-31408 | | 3/2021 | |
| KR | 10-1972236 | | 4/2019 | |
| KR | 20250051558 | | 4/2025 | |
| WO | 2012/014971 | | 2/2012 | |
| WO | WO-2017047962 | A1 * | 3/2017 | A23L 33/135 |
| WO | 2017/179602 | | 10/2017 | |
| WO | 2019/119592 | | 6/2019 | |
| WO | 2019/151843 | | 8/2019 | |
| WO | 2020/050553 | | 3/2020 | |

OTHER PUBLICATIONS

Ganesan et al. Brain, Behavior and Immunity 124 (2025) 9-27.*
Dong-Yun Lee et al. Food Funct., 2021, 12, 10750-10763 Oct. 5, 2021.*
Pearson WR. An introduction to sequence similarity ("homology") searching. Curr Protoc Bioinformatics. Jun. 2013; Chapter 3:3.1.1-3.1.8. doi: 10.1002/0471250953.bi0301s42 (9 pages).*
Toshimitsu et al. Nutrients, Jan. 31, 2020: 12(2):374, 14 pages.*
International Search Report issued Feb. 22, 2022 in International (PCT) Application No. PCT/JP2021/045752.
Monji, Akira, "Special Topic: The forefront of pathophysiological research in psychiatric disorders—The neuroinflammatory hypothesis of psychiatric disorders", Psychiatria Et Neurologia Japonica, 2012, vol. 114, No. 2, pp. 124-133 (cited in ISR and English language translation provided on p. 133).
Zaydi, A.I. et al., "*Lactobacillus plantarum* DR7 improved brain health in aging rats via the serotonin, inflammatory and apoptosis pathways", Beneficial Microbes, 2020, vol. 11, No. 8, pp. 753-766.
Li, Nannan et al., "Oral Probiotics Ameliorate the Behavioral Deficits Induced by Chronic Mild Stress in Mice via the Gut Microbiota-Inflammation Axis", Frontiers in Behavioral Neuroscience, 2018, vol. 12, Article 266, pp. 1-11.
Zolfaghari, Sayyed Iman et al., "The effects of lactobacilli (*L. rhamnosus, L. reuteri, L. Plantarum*) on LPS-induced memory impairment and changes in CaMKII-α and TNF-α genes expression in the hippocampus of rat", Physiology & Behavior, 2021, vol. 229, No. 113224, pp. 1-5.
Hosseinifard, Elaheh-Sadat et al., "The novel insight into anti-inflammatory and anxiolytic effects of psychobiotics in diabetic rats: possible link between gut microbiota and brain regions", European Journal of Nutrition, 2019, vol. 58, No. 8, pp. 3361-3375.

(Continued)

*Primary Examiner* — Oluwatosin A Ogunbiyi
(74) *Attorney, Agent, or Firm* — Wenderoth, Lind & Ponack, L.L.P.

(57) ABSTRACT

A subject is allowed to ingest a composition containing a lactic acid bacterium belonging to the genus *Lactobacillus* to improve inflammation in the brain tissue of the subject.

16 Claims, No Drawings

Specification includes a Sequence Listing.

(56) References Cited

OTHER PUBLICATIONS

Dhaliwal, J. et al., *Lactobacillus plantarum* MTCC 9510 supplementation protects from chronic unpredictable and sleep deprivation-induced behaviour, biochemical and selected gut microbial aberrations in mice, Journal of Applied Microbiology, 2018, vol. 125, pp. 257-269.

Lew, Lee-Ching et al., "Probiotic *Lactobacillus plantarum* P8 alleviated stress and anxiety while ehancing memory and cognition in stressed adults: A randomised, double-bind, placebo-controlled study", Clinical Nutrition, 2019, vol. 38, pp. 2053-2064.

Rudzki, Leszek et al., "Probiotic *Lactobacillus Plantarum* 299v decreases kynurenine concentration and improves cognitive functions in patients with major depression: A double-blind, randomized, placebo controlled study", Psychoneuroendocrinology, 2019, vol. 100, pp. 213-222.

International Preliminary Report on Patentability issued Jun. 13, 2023 in International (PCT) Application No. PCT/JP2021/045752.

Extended European Search Report issued Oct. 30, 2024 in corresponding European Patent Application No. 21906554.7.

T. Toshimitsu et al., "Identification of a *Lactobacillus plantarum* strain that ameliorates chronic inflammation and metabolic disorders in obese and type 2 diabetic mice", Journal of Dairy Science, vol. 99, No. 2, Feb. 2016, pp. 933-946.

T. Toshimitsu et al., "Effects of *Lactobacillus plantarum* strain OLL2712 culture conditions on the anti-inflammatory activities for murine immune cells and obese and type 2 diabetic mice", Applied and Environmental Microbiology, vol. 83, No. 7, Apr. 2017, 11 pages.

Keisuke Sakurai et al., "Effects of *Lactiplantibacillus plantarum* OLL2712 on Memory Function in Older Adults with Declining Memory: A Randomized Placebo-Controlled Trial", Nutrients, vol. 14, No. 20, Oct. 2022, 15 pages.

Taiwan Office Action issued Sep. 4, 2025 in corresponding Taiwan Patent Application No. 110146566, with English machine translation.

Qiu-Jun Wang et al., "Concomitant memantine and Lactobacillus plantarum treatment attenuates cognitive impairments in APPPS1 mice" Aging (Albany NY), vol. 12, No. 1 (Jan. 6, 2020), pp. 628-649.

Japanese Office Action issued Oct. 31, 2025 in corresponding Japanese Patent Application No. 2022-569971, with English translation.

Communication pursuant to Article 94(3) EPC dated Jan. 26, 2026 in corresponding European Patent Application No. 21906554.7.

Decision of Refusal issued Feb. 20, 2026 in corresponding Japanese Patent Application No. 2022-569971, with English language translation.

Rejection Decision of Apr. 20, 2026, in corresponding Taiwan Application No. 110146566, with an English machine translation.

Office Action issued Aug. 13, 2026 in corresponding Chinese Application No. 202180084734.0, with English translation.

* cited by examiner

COMPOSITION FOR IMPROVING INFLAMMATION OF BRAIN TISSUE

CROSS-REFERENCE TO RELATED APPLICATIONS

This application is based upon and claims the benefit of priority from Japanese Patent Application No. 2020-208555 filed Dec. 16, 2020; the entire contents of which are incorporated herein by reference.

BACKGROUND OF THE INVENTION

Field of the Invention

The present invention relates to a composition for improving the inflammation of brain tissue.

Background Art

The brain is the center of the nervous system in animals and is the organ that governs the life activities of animals. It is known that when brain abnormalities occur, not only physical activities but also mental activities may not be performed normally. Inflammation of brain tissue is known to be one of the causes of brain abnormalities, and research into the causes of inflammation and methods for improving inflammation is underway.

Inflammation of brain tissue may affect various brain functions, and may be a factor in brain dysfunction, such as lowering of higher brain functions and the induction of mental disorders and mood disorders (e.g., Non-Patent Document 1).

Meanwhile, although various therapeutic drugs are being researched and developed for these brain dysfunctions, most of them are symptomatic treatments for the causes of organic brain disorders, and the current situation is that they are insufficient as methods for improving or ameliorating these brain dysfunctions.

As an aside, so far, there is knowledge about the relationship between lactic acid bacteria and the improvement of brain functions (e.g., Patent Documents 1 to 3). However, there have been no reports on the relationship between lactic acid bacteria and changes in the amounts of cytokines, especially inflammatory cytokines that cause inflammation in brain tissue. The relationship therebetween has been virtually unknown. In particular, it was not known that the ingestion of lactic acid bacteria could reduce the amounts of inflammatory cytokines in the brain tissue of a subject to ingest and that brain dysfunction, such as deterioration of higher brain functions, mental disorders, and mood disorders could be improved in the subject to ingest.

Inflammation of brain tissue can be a factor in brain dysfunction, such as deterioration of higher brain functions, mental disorders, and mood disorders. Therefore, a method of effectively ameliorating inflammation in brain tissue is desired.

PRIOR ART DOCUMENTS

Patent Documents

Patent Document 1: WO 2017/179602

Patent Document 2: Japanese Unexamined Patent Application Publication (Translation of PCT Application) No. 2018/-531595

Patent Document 3: Japanese Unexamined Patent Application Publication (Translation of PCT Application) No. 2015/-526085

Non-Patent Document

Non-Patent Document 1: Akira Monji, Special Topic: The forefront of pathophysiological research in psychiatric disorders—The neuroinflammatory hypothesis of psychiatric disorders, PSYCHIATRIA ET NEUROLOGIA JAPONICA, Vol. 114, No. 2, pp. 124-133, 2012

An object of the present invention is to provide a composition useful for improving inflammation in a subject, especially a composition useful for improving inflammation in the brain tissue of a subject.

As a result of intensive studies, the present inventors have found that when a lactic acid bacterium belonging to the genus *Lactobacillus* is administered to a subject, the amount of a cytokine suggested to be associated with inflammation can be effectively reduced in the subject, especially in the brain tissue of the subject. The present invention is based on these findings.

According to the present invention, the following inventions are provided.

[1] A composition for suppressing inflammation of a brain tissue, including a lactic acid bacterium belonging to the genus *Lactobacillus.*

[2] The composition according to [1], wherein the brain tissue is hippocampus.

[3] The composition according to [1] or [2], which is for improving a disorder caused by inflammation of the brain tissue.

[4] The composition according to [3], wherein the disorder is at least one disorder selected from the group consisting of a mental disorder and a mood disorder.

[5] The composition according to [3], wherein the disorder is a higher brain dysfunction.

[6] The composition according to [5], wherein the higher brain dysfunction is a disorder of at least one function selected from the group consisting of selective attention function, cognitive function, memory function, executive function, and learning function.

[7] The composition according to [5] or [6], which is for improving a disease caused by the higher brain dysfunction.

[8] The composition according to [7], wherein the disease is selected from the group consisting of Alzheimer's dementia, dementia with Lewy bodies, frontotemporal dementia, amnestic syndrome, generalized attention disorder, social behavior disorder, and memory disorder.

[9] The composition according to any one of [1] to [8], wherein the lactic acid bacterium has an activity of reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in a brain tissue.

[10] The composition according to [9], wherein the brain tissue is hippocampus.

[11] A composition for reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in a brain tissue, the composition including a lactic acid bacterium belonging to the genus *Lactobacillus.*

[12] The composition according to [11], wherein the brain tissue is hippocampus.

[13] A composition for reducing an amount of interleukin-17, the composition including a lactic acid bacterium belonging to the genus *Lactobacillus.*

[14] A composition for improving at least one disorder selected from the group consisting of a mental disorder, a mood disorder, and a higher brain dysfunction, the composition including a lactic acid bacterium belonging to the genus *Lactobacillus.*

[15] The composition according to [14], wherein the higher brain dysfunction is a disorder of at least one function selected from the group consisting of selective attention function, cognitive function, memory function, executive function, and learning function.

[16] The composition according to [14] or [15], which is for improving a disease caused by the higher brain dysfunction.

[17] The composition according to [16], wherein the disease is selected from the group consisting of Alzheimer's dementia, dementia with Lewy bodies, frontotemporal dementia, amnestic syndrome, generalized attention disorder, social behavior disorder, and memory disorder.

[18] The composition according to any one of [1] to [17], wherein the lactic acid bacterium includes a lactic acid bacterium belonging to *Lactobacillus plantarum.*

[19] The composition according to any one of [1] to [18], wherein the lactic acid bacterium has a 16S rRNA gene having a homology of 90% or more to the nucleotide sequence represented by SEQ ID NO: 1.

[20] The composition according to any one of [1] to [19], wherein the lactic acid bacterium is *Lactobacillus plantarum* OLL2712 strain deposited under accession number FERM BP-11262.

[21] The composition according to any one of [1] to [20], wherein the lactic acid bacterium contains an dead bacterial cell of a lactic acid bacterium.

[22] The composition according to any one of [1] to [21], wherein the lactic acid bacterium contains a heat-treated dead bacterial cell.

[23] The composition according to any one of [1] to [22], wherein the composition is a food composition.

[24] The composition according to any one of [1] to [22], wherein the composition is a pharmaceutical composition.

[25] A method of suppressing inflammation in the brain tissue of a subject, the method including allowing the subject to ingest an effective amount of a lactic acid bacterium belonging to the genus *Lactobacillus.*

[26] A method of improving a disorder caused by inflammation in the brain tissue of a subject, the method including allowing the subject to ingest an effective amount of a lactic acid bacterium belonging to the genus *Lactobacillus.*

[27] A method of reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in a brain tissue of a subject, the method including allowing the subject to ingest an effective amount of a lactic acid bacterium belonging to the genus *Lactobacillus.*

[28] A method of improving at least one disorder selected from the group consisting of a mental disorder, a mood disorder, and a higher brain dysfunction in a subject, the method including allowing the subject to ingest an effective amount of a lactic acid bacterium belonging to the genus *Lactobacillus.*

[29] The method according to [28], wherein the higher brain dysfunction is a disorder of at least one function selected from the group consisting of selective attention function, cognitive function, memory function, executive function, and learning function.

[30] The method according to [28] or [29], which is for improving a disease caused by the higher brain dysfunction.

[31] The method according to [30], wherein the disease is selected from the group consisting of Alzheimer's dementia, dementia with Lewy bodies, frontotemporal dementia, amnestic syndrome, generalized attention disorder, social behavior disorder, and memory disorder.

[32] Use of a lactic acid bacterium belonging to the genus *Lactobacillus* for producing a composition for suppressing inflammation in a brain tissue.

[33] The use according to [32], wherein the brain tissue is hippocampus.

[34] The use according to [32] or [33], wherein the composition is a composition for improving a disorder caused by inflammation in the brain tissue.

[35] The use according to [34], wherein the disorder is at least one disorder selected from the group consisting of a mental disorder and a mood disorder.

[36] The use according to [35], wherein the disorder is a higher brain dysfunction.

[37] The use according to [36], wherein the higher brain dysfunction is a disorder of at least one function selected from the group consisting of selective attention function, cognitive function, memory function, executive function, and learning function.

[38] The use according to [36] or [37], wherein the composition is a composition for improving a disease caused by the higher brain dysfunction.

[39] The use according to [38], wherein the disease is selected from the group consisting of Alzheimer's dementia, dementia with Lewy bodies, frontotemporal dementia, amnestic syndrome, generalized attention disorder, social behavior disorder, and memory disorder.

[40] The use of a lactic acid bacterium according to any one of to [39], wherein the lactic acid bacterium has an activity of reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in a brain tissue.

[41] The use of a lactic acid bacterium according to [40], wherein the brain tissue is hippocampus.

[42] Use of a lactic acid bacterium belonging to the genus *Lactobacillus* for producing a composition for reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in a brain tissue.

[43] The use of a lactic acid bacterium according to [42], wherein the brain tissue is hippocampus.

[44] Use of a lactic acid bacterium belonging to the genus *Lactobacillus* for producing a composition for suppressing an amount of interleukin-17.

[45] Use of a lactic acid bacterium belonging to the genus *Lactobacillus* for producing a composition for improving a disorder caused by inflammation in a brain tissue.

[46] Use of a lactic acid bacterium belonging to the genus *Lactobacillus* for producing a composition for improving at least one disorder selected from the group consisting of a mental disorder, a mood disorder, and a higher brain dysfunction, the composition including a lactic acid bacterium belonging to the genus *Lactobacillus.*

[47] The use according to [46], wherein the higher brain dysfunction is a disorder of at least one function selected from the group consisting of selective attention function, cognitive function, memory function, executive function, and learning function.

[48] The use according to [46] or [47], wherein the composition is a composition for improving a disease caused by the higher brain dysfunction.

[49] The use according to [48], wherein the disease is selected from the group consisting of Alzheimer's dementia, dementia with Lewy bodies, frontotemporal dementia, amnestic syndrome, generalized attention disorder, social behavior disorder, and memory disorder.

[50] A lactic acid bacterium belonging to the genus *Lactobacillus* for suppressing inflammation in a brain tissue.

[51] A lactic acid bacterium belonging to the genus *Lactobacillus* for improving a disorder caused by inflammation in a brain tissue.

[52] A lactic acid bacterium belonging to the genus *Lactobacillus* for reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in a brain tissue.

[53] A lactic acid bacterium belonging to the genus *Lactobacillus* for improving at least one disorder selected from the group consisting of a mental disorder, a mood disorder, and a higher brain dysfunction, the composition including a lactic acid bacterium belonging to the genus *Lactobacillus.*

[54] The lactic acid bacterium belonging to the genus *Lactobacillus* according to [53], wherein the higher brain dysfunction is a disorder of at least one function selected from the group consisting of selective attention function, cognitive function, memory function, executive function, and learning function.

[55] The lactic acid bacterium belonging to the genus *Lactobacillus* according to [53] or [54], which is for improving a disease caused by the higher brain dysfunction.

[56] The lactic acid bacterium belonging to the genus *Lactobacillus* according to [55], wherein the disease is selected from the group consisting of Alzheimer's dementia, dementia with Lewy bodies, frontotemporal dementia, amnestic syndrome, generalized attention disorder, social behavior disorder, and memory disorder.

[57] Use of a lactic acid bacterium belonging to the genus *Lactobacillus* for suppressing inflammation in a brain tissue.

[58] Use of a lactic acid bacterium belonging to the genus *Lactobacillus* for improving a disorder caused by inflammation in a brain tissue.

[59] Use of a lactic acid bacterium belonging to the genus *Lactobacillus* for reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in a brain tissue.

[60] Use of a lactic acid bacterium belonging to the genus *Lactobacillus* for improving at least one disorder selected from the group consisting of a mental disorder, a mood disorder, and a higher brain dysfunction, the composition including a lactic acid bacterium belonging to the genus *Lactobacillus.*

[61] Use of the lactic acid bacterium belonging to the genus *Lactobacillus* according to [60], wherein the higher brain dysfunction is a disorder of at least one function selected from the group consisting of selective attention function, cognitive function, memory function, executive function, and learning function.

[62] Use of the lactic acid bacterium belonging to the genus *Lactobacillus* according to [60] or [61], which is for improving a disease caused by the higher brain dysfunction.

[63] Use of the lactic acid bacterium belonging to the genus *Lactobacillus* according to [62], wherein the disease is selected from the group consisting of Alzheimer's dementia, dementia with Lewy bodies, frontotemporal dementia, amnestic syndrome, generalized attention disorder, social behavior disorder, and memory disorder.

According to the present invention, by administering a lactic acid bacterium belonging to the genus *Lactobacillus* to a subject, the amount of a certain cytokine suggested to be associated with inflammation can be effectively reduced in the subject, especially in the brain tissue of the subject. Therefore, the present invention enables to efficiently inhibit inflammation in a subject, especially in the brain tissue of the subject.

DETAILED DESCRIPTION OF THE INVENTION

Composition for Suppressing Inflammation of Brain Tissue

According to one aspect of the present invention, there is provided a composition for suppressing inflammation in the brain tissue, which includes a lactic acid bacterium belonging to the genus *Lactobacillus* (hereinafter, also referred to as "*Lactobacillus* lactic acid bacterium" or "lactic acid bacterium") (hereinafter, also referred to as the "composition according to the present invention").

According to one embodiment of the present invention, the subject to whom the composition of the present invention is applied is not particularly limited as long as the effects of the present invention are exhibited. The subject may be, for example, a mammal such as a human, a monkey, a chimpanzee, a cow, a horse, a sheep, and a goat, and is preferably a human. The applicable subject may be a subject experiencing inflammation, especially a subject experiencing inflammation within the brain tissue, or may be a subject for which the occurrence of inflammation in the brain tissue should be prevented. In one embodiment, when a subject to whom the composition of the present invention is applied is a human, the age of a human as the subject is not particularly limited, but preferably 45 years old or older, more preferably 50 years old or older, still more preferably 60 years old or older, particularly preferably 65 years old or older. In another embodiment, a subject to whom the composition of the present invention is applied can be a human with mild cognitive impairment (MCI). In this case, the age of the human as the subject is not particularly limited.

In the present specification, "brain tissue" means the whole brain or a partial brain region of a subject to whom the composition of the present invention is applied. According to a preferred embodiment of the present invention, the "brain tissue" includes the hippocampus. In other words, according to a preferred embodiment of the present invention, the composition for suppressing inflammation of brain tissue of the present invention is a composition for suppressing inflammation in the hippocampus.

In the present specification, the "suppression" of inflammation encompasses "treatment" and "prevention" of inflammation. The "treatment" of inflammation encompasses not only stopping, alleviating, or delaying the progression or worsening of inflammation by medical intervention, but also stopping, alleviating delaying the progression or worsening of inflammation by non-medical intervention. The "prevention" of inflammation encompasses preparing in advance for an anticipated worsening of inflammation and preventing the occurrence or recurrence of inflammation through medical or non-medical intervention.

According to a preferred embodiment of the present invention, the *Lactobacillus* lactic acid bacterium contained in the composition of the present invention has an activity of reducing the amount of at least one of inflammatory cytokines such as interleukin (IL)-1, IL-6, IL-9, IL-12, IL-17, a granulocyte colony-stimulating factor (G-CSF), a granulocyte monocyte-colony stimulating factor (GM-CSF), interferon-γ (IFN-γ), monocyte chemoattractant protein-1 (MCP-1), macrophage inflammatory protein-1 (MIP-1), and tumor necrosis factor-α (TNF-α). According to another preferred embodiment, the *Lactobacillus* lactic acid bacterium contained in the composition of the present invention has an activity of reducing the amount of at least one of the above-described inflammatory cytokines in the brain tissue. Further, according to another embodiment, the *Lactobacillus* lactic acid bacterium contained in the composition of the present invention has an activity of reducing the amount of at least one of the above-described inflammatory cytokines in the hippocampus.

In the present specification, the expression "having an activity of reducing" used regarding an inflammatory cytokine means that when a subject is stimulated with a lactic acid bacterium belonging to the genus *Lactobacillus* or a composition containing the lactic acid bacterium, the amount of an inflammatory cytokine in the stimulated subject, especially in the brain tissue of the subject, tends to decrease, preferably decreases statistically significantly (namely, above the range of error) as compared to that in a subject who received no stimulation. The measurement of the amount of an inflammatory cytokine and the determination of the presence or absence of activity of reducing the amount of an inflammatory cytokine can be performed by, for example, the methods shown in the Examples. The statistical analysis of the amount of an inflammatory cytokine can be carried out by a statistical analysis method known to those skilled in the art. Specifically, the statistical analysis of the amount of an inflammatory cytokine can be carried out by t-test.

As the composition for suppressing inflammation of brain tissue of the present invention can effectively suppress inflammation in the brain tissue, it can be used for improving a disorder or a disease caused by inflammation in the brain tissue, especially a disorder or a disease caused by inflammation in the hippocampus. Therefore, according to another aspect of the present invention, there is provided a composition for improving a disorder or a disease caused by inflammation of brain tissue, such as a higher brain dysfunction, a mental disorder, or a mood disorder as described later.

Composition for Improving Higher Brain Dysfunction

According to one aspect of the present invention, there is provided a composition for improving a decline in higher brain function (namely, higher brain dysfunction), which includes a lactic acid bacterium belonging to the genus *Lactobacillus*.

A subject to whom the composition for improving a higher brain dysfunction of the present invention is applied can be the same as described for the composition for suppressing inflammation of brain tissue of the present invention. In addition, the subject to whom the composition is applied may be a subject with a normal higher brain function or a subject with a decline in higher brain function (having a disorder in higher brain function).

In the present specification, the expression "improving a higher brain dysfunction" encompasses not only the meaning of "improvement of higher brain function" but also the meaning of "maintenance of higher brain function" and "prevention of declined higher brain function" The "improvement of higher brain function" encompasses the promotion of recovery of higher brain function from a state in which higher brain function has declined due to inflammation associated with aging and brain diseases (e.g., cerebral infarction, ischemic stroke such as transient cerebral ischemic attack, hemorrhagic stroke such as cerebral hemorrhage or subarachnoid hemorrhage, traumatic diseases such as concussion and brain contusion) and the like. The "maintenance of higher brain function" encompasses the maintenance of healthy higher brain function and the like. The "prevention of a decline in higher brain function" encompasses the prevention of a decline in higher brain function in a healthy state, the prevention of further reduction in the declined higher brain function, and the like. Examples of a higher brain function include selective attention function, cognitive function, memory function, executive function, learning function, verbal function, and calculation function. Examples of a disorder caused by a decline in higher brain function include hemiasomatognosia, topographical disturbance, agnosia, aphasia, memory disorder, mild cognitive disorder, apraxia, attention disorder, executive dysfunction, and behavioral or emotional disorder.

The composition for improving higher brain dysfunction of the present invention can improve higher brain dysfunction and thus can be used for improving a disease caused by higher brain dysfunction. Examples of a disease caused by higher brain dysfunction include dementias such as Alzheimer's dementia, dementia with Lewy bodies, and frontotemporal dementia, amnestic syndrome, generalized attention disorder, social behavior disorder, and memory disorder. In the present specification, the "improvement" of a disease or disorder encompasses "treatment" and "prevention" of a disease or disorder. The "treatment" of a disease or disorder encompasses not only stopping, alleviating, or delaying the progression or worsening of a disease or disorder by medical intervention, but also stopping, alleviating, delaying the progression or worsening of a disease or disorder by non-medical intervention. The "prevention" of a disease or disorder encompasses preparing in advance for an anticipated worsening of a disease or disorder and preventing the occurrence or recurrence of a disease or disorder through medical or non-medical intervention.

According to a preferred embodiment of the present invention, the composition for improving higher brain dysfunction of the present invention is a composition for improving higher brain dysfunction, treating higher brain dysfunction, preventing higher brain dysfunction, ameliorating higher brain function, improving higher brain function, maintaining higher brain function, preventing a decline in higher brain function, improving a disease or disorder caused by declined higher brain function (e.g., dementias such as Alzheimer's dementia, dementia with Lewy bodies, and frontotemporal dementia, amnestic syndrome, generalized attention disorder, social behavior disorder, and memory disorder), treating a disease or disorder caused by declined higher brain function, preventing a disease or disorder caused by declined higher brain function, ameliorating cognitive function, improving cognitive function, suppressing a decline in cognitive function, suppressing an increase in the dementia risk, reducing the dementia risk, improving memory function, maintaining memory function, and suppressing a decline in memory function.

Composition for Improving Mental Disorder

According to another aspect of the present invention, there is provided a composition for improving a mental disorder, which includes a lactic acid bacterium belonging to the genus *Lactobacillus*.

A subject to whom the composition for improving a mental disorder of the present invention is applied can be the same as described for the composition for suppressing inflammation of brain tissue of the present invention. In addition, the subject to whom the composition is applied may be a subject with a normal (healthy) mental function (mental state) (namely, without a disorder in mental function) or a subject with an abnormal mental function (namely, with a disorder in mental function).

Mental disorders are also called "mental diseases," and although there is no uniform definition, they are defined as, for example, psychological syndromes accompanied by distress and abnormalities. As mental disorders, for example, among the classifications F09-F99 in Chapter V, "Mental and behavioural disorders" in "International Statistical Classification of Diseases and Related Health Problems, 10th revision" of the World Health Organization (WHO), F30-F39 refer to disorders classified other than "mood (emotional) disorders" Specific examples thereof include disorders and diseases such as schizophrenia, epilepsy, panic disorder, obsessive-compulsive disorder, generalized anxiety disorder, post-traumatic stress disorder, intellectual disability, personality disorder, eating disorder, sleep disorder, and adjustment disorder.

In the present specification, "improving mental disorder" encompasses not only the meaning of "treatment of mental disorder" but also the meaning of "prevention of mental disorder" In addition, the "treatment of mental disorder" encompasses the promotion of recovery of a mental disorder occurring due to inflammation associated with aging and brain diseases (e.g., cerebral infarction, ischemic stroke such as transient cerebral ischemic attack, hemorrhagic stroke such as cerebral hemorrhage or subarachnoid hemorrhage, traumatic diseases such as concussion and brain contusion) and the like. In addition, "prevention of mental disorder" encompasses the maintenance of a normal mental function, prevention of further disorder from an impaired mental function, and the like.

According to a preferred embodiment of the present invention, the composition for improving a mental disorder of the present invention is a composition for improving a mental disorder, treating a mental disorder, preventing a mental disorder, treating schizophrenia, epilepsy, panic disorder, obsessive-compulsive disorder, generalized anxiety disorder, post-traumatic stress disorder, intellectual disability, personality disorder, eating disorder, sleep disorder, and/or adjustment disorder, or preventing schizophrenia, epilepsy, panic disorder, obsessive-compulsive disorder, generalized anxiety disorder, post-traumatic stress disorder, intellectual disability, personality disorder, eating disorder, sleep disorder, and/or adjustment disorder.

Composition for Improving Mood Disorder

According to another aspect of the present invention, there is provided a composition for improving a mood disorder, which includes a lactic acid bacterium belonging to the genus *Lactobacillus*.

A subject to whom the composition for improving a mood disorder of the present invention is applied can be the same as described for the composition for suppressing inflammation of brain tissue of the present invention. In addition, the subject to whom the composition is applied may be a subject with a normal (healthy) mood state (emotional state) (namely, without a disorder in a mood state) or a subject with an abnormal mood state (namely, with a disorder in a mood state).

Mood disorders are also called "emotional disorders" and refer to mental disorders specifically related to mood. There is no unified definition of mood disorder, but it is defined as a state in which, for example, mood (emotion) changes that persist for a certain period cause pain or interfere with daily life. As mood disorders, for example, among the classifications in Chapter V, "Mental and behavioural disorders" in "International Statistical Classification of Diseases and Related Health Problems, 10th revision" of WHO, F30-F39 refer to disorders classified as "mood (emotional) disorders" More specific examples thereof include disorders and diseases such as depression, mania, bipolar disorder, mixed episodes, and substance-induced mood disorders.

In the present specification, "improving mood disorder" encompasses not only the meaning of "treatment of mood disorder" but also the meaning of "prevention of mood disorder" In addition, the "treatment of mood disorder" encompasses the promotion of recovery of a mood disorder occurring due to inflammation associated with aging and brain diseases (e.g., cerebral infarction, ischemic stroke such as transient cerebral ischemic attack, hemorrhagic stroke such as cerebral hemorrhage or subarachnoid hemorrhage, traumatic diseases such as concussion and brain contusion) and the like. In addition, "prevention of mood disorder" encompasses the maintenance of a normal mood state, prevention of further disorder from an impaired mood state, and the like.

According to a preferred embodiment of the present invention, the composition for improving a mood disorder of the present invention is a composition for improving a mood disorder, treating a mood disorder, preventing a mood disorder, improving depression, treating depression, preventing depression, suppressing an increase in the depression risk, reducing the depression risk, improving mania, improving bipolar disorder, improving a mixed episode, or improving a substance-induced mood disorder.

Composition for Reducing Amount of Inflammatory Cytokine

According to another aspect of the present invention, there is provided a composition for reducing the amount of an inflammatory cytokine, which includes a lactic acid bacterium belonging to the genus *Lactobacillus*. According to a preferred embodiment, the composition for reducing the amount of an inflammatory cytokine of the present invention reduces the amount of an inflammatory cytokine in the brain tissue. According to a more preferred embodiment, the composition for reducing the amount of an inflammatory cytokine of the present invention reduces the amount of an inflammatory cytokine in the hippocampus.

Examples of an inflammatory cytokine whose amount is reduced with the composition for reducing the amount of an inflammatory cytokine of the present invention include IL-1, IL-6, IL-9, IL-12, IL-17, G-CSF, GM-CSF, IFN-γ, MCP-1, MIP-1, and TNF-α. In other words, according to a preferred embodiment, the composition for reducing the amount of an inflammatory cytokine of the present invention reduces the amount of at least one of these inflammatory cytokines. According to a preferred embodiment, the composition for reducing the amount of an inflammatory cytokine of the present invention reduces the amount of IL-17.

According to a preferred embodiment, the composition for reducing the amount of an inflammatory cytokine of the present invention is a composition for suppressing the production of an inflammatory cytokine in the brain tissue, especially a composition for suppressing the production of an inflammatory cytokine in the hippocampus.

Examples of a cytokine whose production is suppressed with the composition for suppressing the production of an inflammatory cytokine of the present invention are the same as the inflammatory cytokines described above. In other words, according to a preferred embodiment, the composition for suppressing the production of an inflammatory cytokine of the present invention reduces the production of at least one of the inflammatory cytokines described above. According to a preferred embodiment, the composition for suppressing the production of an inflammatory cytokine of the present invention suppresses the production of IL-17.

Examples of the *Lactobacillus* lactic acid bacterium contained in the composition of the present invention include *Lactobacillus delbrueckii* subsp. *burgaricus, Lactobacillus delbrueckii* subsp. *lactis, Lactobacillus casei, Lactobacillus helveticus, Lactobacillus acidophilus, Lactobacillus crispatus, Lactobacillus amylovorus, Lactobacillus gallinarum, Lactobacillus gasseri, Lactobacillus oris, Lactobacillus rhamnosus, Lactobacillus johnsonii, Lactobacillus fermentum, Lactobacillus brevis, Lactobacillus plantarum, Lactobacillus pentosus, Lactobacillus paraplantarum, Lactobacillus paracollinoides, Lactobacillus hammesii*. Among these *Lactobacillus* lactic acid bacteria, *Lactobacillus plantarum* is preferably used, and *Lactobacillus plantarum* strain OLL2712 is more preferably used. In the present specification, "the lactic acid bacterium belonging to the genus *Lactobacillus*" refers to a lactic acid bacterium belonging to any one of 25 genera newly established by the reorganization of lactic acid bacteria, announced in the paper "A taxonomic note on the genus *Lactobacillus*: Description of 23 novel genera, emended description of the genus *Lactobacillus* Beijerinck 1901, and union of Lactobacilliae and Leuconostocaceae" in INTERNATIONAL JOURNAL OF SYSTEMATIC AND EVOLUTIONARY MICROBIOLOGY, Volume 70, Issue 4, published Apr. 15, 2020. The 25 genera are, namely the genera *Lactobacillus, Paralactobacillus, Holzapfelia, Amylolactobacillus, Bombilactobacillus, Companilactobacillus, Lapidilactobacillus, Agrilactobacillus, Schleiferilactobacillus, Loigolactobacilus, Lacticaseibacillus, Latilactobacillus, Dellaglioa, Liquorilactobacillus, Ligilactobacillus, Lactiplantibacillus, Furfurilactobacillus, Paucilactobacillus, Limosilactobacillus, Fructilactobacillus, Acetilactobacillus, Apilactobacillus, Levilactobacillus, Secundilactobacillus* and *Lentilactobacillus*. Among the lactic acid bacteria belonging to the genera after the reorganization described above, a lactic acid bacterium belonging to any of the genera *Lactobacillus, Lacticaseibacillus, Lactiplantibacillus, Liquorilactobacillus, Limosilactobacillus* and *Levilactobacillus* is preferably used in the present invention. It is noted, that conventional *Lactobacillus plantarum* is classified as the genus *Lactiplantibacillus* by the classification after the above-described reorganization, and called *Lactiplantibacillus plantarum.*

The *Lactobacillus plantarum* OLL2712 strain is deposited at the Patent organism Depositary in the National Institute of Advanced Industrial Science and Technology (Central 6, 1-1-1 Higashi, Tsukuba, Ibaraki, Japan) on Jul. 2, 2010, then transferred to the International Depositary under accession number FERM BP-11262. As described in Budapest Notification No. 282 (www.wipo.int), the National Institute of Technology and Evaluation (IPOD, NITE) has taken over the patent microorganism deposition services from the International Patent Organism Depositary of the National Institute of Advanced Industrial Science and Technology (IPOD, AIST), and therefore the *Lactobacillus plantarum* OLL2712 strain is now deposited at National Institute of Technology and Evaluation (IPOD, NITE) (#120, 2-5-8 Kazusakamatari, Kisarazu-shi, Chiba, Japan) under accession number FERM BP-11262.

As the *Lactobacillus* lactic acid bacterium to be contained in the composition of the present invention, a strain substantially equivalent to the above-described deposited strain can also be used. It is an unexpected fact to those skilled in the art that the above-described deposited strain or a substantially equivalent strain can reduce the amount of an inflammatory cytokine in the brain tissue, especially in the hippocampus. The "substantially equivalent strain" refers to, for example, a strain of the above-described *Lactobacillus* lactic acid bacterium, the strain having the 16S rRNA gene whose nucleotide sequence has a homology of 90% or more, preferably 95% or more, more preferably 98% or more, and still more preferably 99% or more to the nucleotide sequence (SEQ ID NO: 1) of the 16S rRNA gene of the above-described deposited strain, and preferably having the same mycological properties identical to those of the above-described strain. A strain having the same mycological properties is preferably a strain having an activity similar to that of the above-described deposited strain in that it has an activity to decrease the amount of an inflammatory cytokine in the brain tissue, especially in the hippocampus in a subject (e.g., human) Further, the *Lactobacillus* lactic acid bacterium to be contained in the composition of the present invention may be a strain bred from the deposited strain or from a strain substantially equivalent thereto, by mutation treatment, genetic recombination, selection of a natural mutant, etc., as long as the effects of the present invention are exhibited.

Examples of the *Lactobacillus* lactic acid bacterium to be contained in the composition of the present invention include, in addition to the bacterial cells themselves of the *Lactobacillus* lactic acid bacterium, a culture containing the bacterial cells of the *Lactobacillus* lactic acid bacterium. As the bacterial cells of the *Lactobacillus* lactic acid bacterium, both live bacterial cells and dead bacterial cells can be used. However, dead bacterial cells are preferred, and dead bacterial cells obtained by heat-treating the live bacterial cells (heat-treated dead bacterial cells) are more preferred. That is, the *Lactobacillus* lactic acid bacterium to be contained in the composition of the present invention preferably includes dead bacterial cells, and more preferably includes heat-treated dead bacterial cells. The number of passages of the *Lactobacillus* lactic acid bacterium is not particularly limited as long as the effects of the present invention are exhibited, but is, for example, from 1 to 30, preferably from 5 to 15, and more preferably from 11 to 13.

Culturing conditions for the *Lactobacillus* lactic acid bacterium are not particularly limited as long as the effects of the present invention are exhibited, and conditions usually used for culturing lactic acid bacteria can be used. For example, it is possible to use, as a medium, a medium obtained by: dissolving whey powder and a whey protein concentrate in sterile water; digesting the solution with protease A; then adding thereto a yeast extract, a fish extract and $MnSO_4$, and further adding various nutrients (vitamins, minerals, and fatty acid esters); adjusting the pH to 6.7 with NaOH, followed by autoclaving for sterilization. The pH during the culture can be adjusted within the range of from 4.8 to 6.8. $K_2CO_3$ can be used to adjust the pH. The temperature during the culture can be adjusted within the range of from 29 to 40° C.

The heat treatment for obtaining the heat-treated dead bacterial cells of the *Lactobacillus* lactic acid bacterium is not particularly limited as long as the effects of the present invention are exhibited, and is carried out under the conditions usually used for sterilizing lactic acid bacteria.

As the *Lactobacillus* lactic acid bacterium, it is possible to use one which has been subjected to concentration or dilution, freezing, drying, powdering, and/or the like, in addition to the heat treatment described above.

As the *Lactobacillus* lactic acid bacterium to be contained in the composition of the present invention, a bacterium prepared by the above-described culture and/or any of various treatments, or a commercially available composition containing the *Lactobacillus* lactic acid bacterium may be used.

In the composition of the present invention, the number of bacterial cells of the *Lactobacillus* lactic acid bacterium per mass of the composition is not particularly limited as long as the effects of the present invention are exhibited. However, the number of bacterial cells is preferably from $10^6$ to $10^{13}$ cells/g, more preferably from $10^6$ to $1\times10^{12}$ cells/g, still more preferably from $10^7$ to $10^{11}$ cells/g, yet still more preferably from $10^8$ to $10^{11}$ cells/g, and particularly preferably from $10^8$ to $10^{10}$ cells/g. Further, in the composition of the present invention, the dry mass of bacterial cells per mass of the solid content in the composition is preferably from 0.01 to 100% by mass, more preferably from 1 to 80% by mass, and still more preferably 10 to 40% by mass.

The composition of the present invention may contain components other than the *Lactobacillus* lactic acid bacterium as long as they do not interfere with the effects of the invention of the present application. Examples of the component other than the *Lactobacillus* lactic acid bacterium include medium components, additives suitable for oral ingestion or tube feeding, solvents such as water, carbohydrates, proteins, lipids, vitamins, minerals, bio-essential trace metals (manganese sulfate, zinc sulfate, magnesium chloride, potassium carbonate, etc.), flavorings, carriers acceptable in terms of food hygiene or acceptable pharmaceutically, and food additives.

Examples of the carbohydrate include sugars, processed starches (dextrin, soluble starch, british starch, oxidized starch, starch esters, starch ethers, etc.), and dietary fiber.

Examples of proteins include: animal and vegetable proteins such as whole milk powder, skimmed milk powder, partially skimmed milk powder, casein, whey powder, whey proteins, whey protein concentrates, whey protein isolates, α-casein, β-casein, κ-casein, β-lactoglobulin, α-lactalbumin, lactoferrin, soy proteins, egg proteins and meat proteins; hydrolyzed products of these proteins; and various milk-derived components such as butter, milk minerals, cream, whey, non-protein nitrogen, sialic acid, phospholipids and lactose.

Examples of lipids include: animal fats and oils such as lard and fish oils, and fractionated, hydrogenated and transesterification oils thereof; and vegetable fats and oils such as palm oil, safflower oil, corn oil, rapeseed oil and coconut oil, and fractionated, hydrogenated and transesterification oils thereof.

Examples of vitamins include vitamin A, carotenes, vitamin B-complex, vitamin C, vitamin D-complex, vitamin E, vitamin K-complex, vitamin P, vitamin Q, niacin, nicotinic acid, pantothenic acid, biotin, inositol, choline, and folic acid.

Examples of minerals include calcium, potassium, magnesium, sodium, copper, iron, manganese, zinc, and selenium.

The composition of the present invention can be produced by incorporating a lactic acid bacterium belonging to the genus *Lactobacillus*, and in addition, a pharmaceutically acceptable carrier and/or additives, a carrier acceptable in terms of food hygiene and/or additives, etc., as described above. Therefore, according to one aspect of the present invention, there is provided a method of producing a composition for suppressing inflammation of brain tissue, the method including the step of incorporating a lactic acid bacterium belonging to the genus *Lactobacillus*. In addition, according to another aspect of the present invention, there is provided a method of producing a composition for improving a higher brain dysfunction, a composition for improving a mental disorder, or a composition for improving a mood disorder, the method including the same step described above.

According to a preferred embodiment of the present invention, the composition of the present invention contains fermented milk in addition to a lactic acid bacterium belonging to the genus *Lactobacillus*. It is particularly advantageous to allow a subject to ingest a lactic acid bacterium belonging to the genus *Lactobacillus* with fermented milk to reduce the amount of a cytokine suggested to be associated with inflammation in the brain tissue, such as the hippocampus. Such fermented milk is not particularly limited as long as the effects of the present invention are exhibited, but examples thereof include a set-type yogurt (set yogurt, solid fermented milk), a stirred yogurt (paste-like fermented milk), a drink yogurt (liquid fermented milk), and a frozen yogurt.

According to an embodiment of the present invention, the composition of the present invention can be provided as a food composition. The food composition of the present invention can be any form of food that can contain the lactic acid bacterium, and can be in any form that can be ingested orally or by tube, such as solution, suspension, emulsion, powder, paste, semi-solid molding, and solid molding. Specific examples of the food include solid or semi-solid foods (bread, crackers, pizza crust, yogurt, cheese, formula milk, and the like), drinks (dairy drinks (milk, lactic acid bacteria beverages, lactic beverage) and the like), liquid diet, foods for the sick, nutritional foods, frozen foods, processed food, sweets (chocolate, tablets (tablet type candy), gummies, jell, candy, biscuits, ice cream, frozen sweets, and the like), seasonings, and other commercially available foods. Dairy products containing lactic acid bacteria (dairy drinks, yogurt, and the like) are preferable.

The food compositions of the present invention can be food and beverage products indicated for the following uses: for suppression of inflammation occurring in the brain tissue, for improvement of inflammation occurring in the brain tissue, for suppression of the occurrence of inflammation in the brain tissue, for suppression of the production of an inflammatory cytokine in the brain tissue, for suppression of inflammation occurring in the hippocampus, for improvement of inflammation occurring in the hippocampus, for suppression of the occurrence of inflammation in the hippocampus, for suppression of the production of an inflammatory cytokine in the hippocampus, for amelioration of higher brain function, for improvement of higher brain function, for maintenance of higher brain function, for suppression of a decline in higher brain function, for improvement of a disease or disorder due to declined higher brain function, for improvement of a mental disorder, for prevention of a mental disorder, for improvement of a mood disorder, for prevention of a mood disorder, and the like. Specifically, the food and beverage products can be indicated for the following uses: "for suppression of inflammation in the brain tissue," "for improvement of inflammation in the brain tissue," "for suppression of the occurrence of inflammation in the brain tissue," "for suppression of the production of an inflammatory cytokine in the brain tissue," "for suppression of inflammation in the hippocampus," "for improvement of inflammation in the hippocampus," "for suppression of the occurrence of inflammation in the hippocampus," "for suppression of the production of an inflammatory cytokine in the hippocampus," "for amelioration of higher brain function," "for improvement of higher brain function," "for maintenance of higher brain function," "for suppression of a decline in higher brain function," "for improvement of a disease or disorder due to declined higher brain function," "for improvement of a mental disorder," "for prevention of a mental disorder," "for improvement of a mood disorder," "for prevention of a mood disorder," "for improvement of cognitive function," "for suppression of declined (decreased) cognitive function," "for support of cognitive function," "for reduction of the dementia risk," "for improvement of accuracy of memory function (or memory ability)," "for improvement of memory function (or memory ability)," "for maintenance of memory function (or memory ability)," "for suppression of declined (decreased) memory function (or memory ability)," "for support of memory function (or memory ability)," "for prevention of memory loss," "for improvement of memory loss," "maintenance of attentiveness," "for improvement of depression," "for prevention of depression," "for reduction of the depression risk," "for maintenance of positive mood (having clear head, feeling vividly, being in a proactive mood, feeling high energy, or the like)," etc. Other indications can be used as well, as long as they indicate the effect produced by suppression of brain tissue inflammation (e.g., suppression of hippocampal inflammation), reduction of the amount of an inflammatory cytokine in the brain tissue (suppression of the production), or reduction of the amount of an inflammatory cytokine in the hippocampus (suppression of the production). For each of the uses mentioned above, "memory" includes the ability to encode (memorize), store (retain), retrieve (recall), and manipulate (process) information. In addition, examples of "memory function" or "memory ability" include the ability to memorize words (verbal memory ability), the ability to memorize numbers (numerical memory ability), the ability to memorize space (spatial perception ability, and spatial cognitive ability; for example, the ability to grasp a two-dimensional or three-dimensional position). In addition, although "memory function" or "memory ability" includes both long-term and short-term memory function or ability, the composition of the present invention may contribute particularly significantly to short-term memory function or ability.

In this specification, "indication" means all actions to notify consumers of the above-described use, and any indication that may evoke or analogize the above-described use can be considered as "indication" used in the present invention, regardless of the purpose of the indication, the content of the indication, the object and medium of the indication, etc. However, it is preferable to indicate with expressions that enable consumers to directly recognize the above-mentioned uses. However, it is preferred to use expressions that allow consumers to directly recognize the above-mentioned use, for the indication.

It is preferable that the indication be an indication that is authorized by the government, etc. (e.g., authorized based on various systems established by the government and indicated in a manner based on such authorization). Examples include an indication as health foods, functional foods, foods with functional claims, enteral foods, foods for special dietary uses, foods for the sick, food with nutrient function claims, quasi-pharmaceutical products, and the like; other indications approved by the Health Labor and Welfare Ministry such as food for specified health use; and indications approved by similar systems. Examples of the latter include an indication as a food for specified health use, an indication as a qualified food for specified health use, an indication for the effect that the product affects the structure and function of the body, and an indication for reducing the risk of disease. More specifically, examples include an indication as a food for specified health use (especially, an indication for health use) prescribed by Ordinance for Enforcement of Health Promotion Act (Apr. 30, 2003, Japan Ministry of Health, Labor and Welfare Ordinance No. 86), and a similar indication.

According to another aspect of the present invention, the composition of the present invention can be provided as a pharmaceutical composition. The pharmaceutical composition of the present invention can be produced according to the ordinary producing procedure of the food product except that it contains lactic acid bacteria. The term "pharmaceutical composition" used herein means the composition of the present invention prepared as an oral formulation or a parenteral formulation according to a conventional method. The formulation may be accompanied by additives acceptable for formulation. Examples of additives acceptable for formulation include excipients, stabilizers, preservatives, wetting agents, emulsifiers, lubricants, sweeteners, colorants, flavorings, buffers, antioxidants, and pH adjusters. When the pharmaceutical composition is an oral formulation, the composition can be prepared as a solid formulation such as a tablet, a powder, a fine granule, a granule, a capsule or a sustained-release agent, or a liquid formulation such as a solution, a suspension, or an emulsion. When the pharmaceutical composition is a parenteral formulation, the composition can be prepared as an injection, a suppository, or the like. From the viewpoint of simplicity of ingestion (administration) to a subject to ingest, the pharmaceutical composition is preferably an oral preparation.

The amount of the composition of the present invention to be ingested is not particularly limited as long as the effects of the present invention are exhibited, and can be appropriately adjusted according to age, health condition, body weight, and the like of the subject to ingest. Typically, the amount of the composition is from 0.001 to 10 g/kg body weight, preferably from 0.01 to 7 g/kg body weight, more preferably from 0.5 to 5 g/kg body weight, and still more preferably from 1 to 2 g/kg body weight, per day. The dry mass of the lactic acid bacterium is preferably 0.001 to 1000 mg/kg body weight, more preferably 0.01 to 100 mg/kg body weight, more preferably 0.05 to 30 mg/kg body weight, and even more preferably 0.1 to 10 mg/kg body weight. The number of bacterial cells of the lactic acid bacterium is preferably from $10^4$ to $10^{12}$ cells/kg body weight, more preferably from $10^5$ to $10^{11}$ cells/kg body weight, still more preferably from $10^6$ to $10^{10}$ cells/kg body weight, and particularly preferably from $10^6$ to $10^8$ cells/kg body weight.

The composition of the present invention is preferably continuously ingested (administered) over a long period of time, specifically, continuously ingested (administered) for 3 days or more, and more preferably continuously ingested (administered) for 1 week or more, more, in order to exert its effect better. Examples of the ingestion (administration) period include 1 to 6 weeks, 1 to 12 weeks, 2 to 10 weeks, 4 to 10 weeks, and 4 to 12 weeks. As used herein, "continuously" means continuing to ingest a predetermined amount of the composition of the present invention daily.

According to another aspect of the present invention, there is provided a method of suppressing inflammation in the brain tissue of a subject, the method including allowing the subject to ingest an effective amount of a lactic acid bacterium belonging to the genus *Lactobacillus*. According to a preferred embodiment, there is provided a method of suppressing hippocampal inflammation in a subject, the method including allowing the subject to ingest an effective amount of a lactic acid bacterium belonging to the genus *Lactobacillus*. The above-described method may be a non-therapeutic method, or may be a therapeutic method.

In addition, the subject to ingest the lactic acid bacterium is not particularly limited as long as it is a subject that needs to suppress inflammation in brain tissue, and may be a healthy individual, an individual experiencing inflammation in brain tissue, or an individual who should prevent the occurrence of inflammation in brain tissue.

In the method of suppressing inflammation in brain tissue, an amount and period of the ingestion of the above-described lactic acid bacterium are not particularly limited as long as the effects of the present invention are exhibited, and can be appropriately adjusted according to age, health condition, body weight, and the like of the subject to ingest. Typically, in the method of the present invention, the amount and period of the ingestion of the above-described lactic acid bacterium are similar to the amount and period of the lactic acid bacterium in the composition of the present invention.

As described above, since inflammation in the brain tissue, especially in the hippocampus, can be suppressed by allowing a subject to ingest an effective amount of a lactic acid bacterium belonging to The genus *Lactobacillus*, another aspect of the present invention provides a method of improving a disorder or a disease caused by inflammation in the brain tissue of the subject, the method including allowing the subject to ingest an effective amount of a lactic acid bacterium belonging to The genus *Lactobacillus*. Examples of a disorder caused by inflammation in the brain tissue include deterioration of a higher brain function, a mental disorder, and a mood disorder. Therefore, according to another aspect of the present invention, there is provided a method of improving a higher brain dysfunction, a method of improving a mental disorder, or a method of improving a mood disorder, the method including the same step as the above-described method of suppressing inflammation in the brain tissue. According to a preferred embodiment, there is provided a method of improving a higher brain dysfunction, a method of improving a mental disorder, or a method of improving a mood disorder, the method including the same step as the above-described method of suppressing inflammation in the hippocampus.

According to another aspect of the present invention, there is provided a method of reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in a brain tissue, especially in the hippocampus of a subject, the method including allowing the subject to ingest an effective amount of a lactic acid bacterium belonging to the genus *Lactobacillus*.

According to another aspect of the present invention, there is provided the use of a lactic acid bacterium belonging to the genus *Lactobacillus* for suppressing inflammation in the brain tissue. According to a preferred embodiment, there is provided the use of a lactic acid bacterium belonging to the genus *Lactobacillus* for suppressing inflammation in the hippocampus. In addition, as described above, since inflammation in the brain tissue, especially in the hippocampus, can be suppressed with a lactic acid bacterium belonging to the genus *Lactobacillus*, another aspect of the present invention provides the use of a lactic acid bacterium belonging to the genus *Lactobacillus* for improving a disorder caused by inflammation in the brain tissue. According to a more preferred embodiment, the lactic acid bacterium is provided as a food composition. According to another more preferred embodiment, the lactic acid bacterium is ingested by a subject by a non-therapeutic method.

According to another aspect of the present invention, there is provided the use of a lactic acid bacterium belonging to the genus *Lactobacillus* for improving a higher brain dysfunction, improving a mental disorder, or improving a mood disorder, According to another aspect of the present invention, there is provided the use of a lactic acid bacterium belonging to the genus *Lactobacillus* for reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in a brain tissue, especially in the hippocampus.

According to another aspect of the present invention, there is provided the use of a lactic acid bacterium belonging to the genus *Lactobacillus* for producing a composition for suppressing inflammation in the brain tissue. According to a preferred embodiment, there is provided the use of a lactic acid bacterium belonging to the genus *Lactobacillus* for producing a composition for suppressing inflammation in the hippocampus. According to another aspect, there is provided the use of a lactic acid bacterium belonging to the genus *Lactobacillus* for producing a composition for improving a disorder caused by inflammation in the brain tissue. According to a more preferred embodiment, the lactic acid bacterium is used for producing a food composition or a pharmaceutical composition. As described above, since a composition for suppressing inflammation can be provided as a pharmaceutical composition, another aspect of the present invention provides the use of a lactic acid bacterium belonging to the genus *Lactobacillus* for producing a medicine for suppressing inflammation in the brain tissue, especially in the hippocampus. In addition, another aspect provides the use of a lactic acid bacterium belonging to the genus *Lactobacillus* for producing a medicine for improving a disorder caused by inflammation in the brain tissue.

According to another more preferred embodiment, the lactic acid bacterium is ingested by a subject by a non-therapeutic method.

According to another aspect of the present invention, there is provided the use of a lactic acid bacterium belonging to the genus *Lactobacillus* for producing a composition for improving a higher brain dysfunction, a composition for improving a mental disorder, or a composition for improving a mood disorder. In a preferred embodiment, the lactic acid bacterium is used for producing a food composition or a pharmaceutical composition. As described above, since each of these compositions can be provided as a pharmaceutical composition, another aspect of the present invention provides the use of a lactic acid bacterium belonging to the genus *Lactobacillus* for producing a medicine for improving a higher brain dysfunction, a mental disorder, or a mood disorder.

According to another aspect of the present invention, there is provided the use of a lactic acid bacterium belonging to the genus *Lactobacillus* for producing a composition for reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in a brain tissue, especially in the hippocampus. In a preferred embodiment, the lactic acid bacterium is used for producing a food composition or a pharmaceutical composition. As described above, since the composition for reducing the amount of an inflammatory cytokine in the brain tissue, especially in the hippocampus, can be provided as a pharmaceutical composition, another aspect of the present invention provides the use of a lactic acid bacterium belonging to the genus *Lactobacillus* for producing a medicine for reducing the amount of an inflammatory cytokine in the brain tissue, especially in the hippocampus.

According to another aspect of the present invention, there is provided a method of suppressing inflammation or reducing a risk of the occurrence of inflammation in the brain tissue of a subject, the method including administering a lactic acid bacterium belonging to the genus *Lactobacillus* to the subject. According to a preferred embodiment, there is provided a method of suppressing inflammation or reducing a risk of the occurrence of inflammation in the hippocampus of a subject, the method including administering a lactic acid bacterium belonging to the genus *Lactobacillus* to the subject. According to a more preferred embodiment, the lactic acid bacterium is ingested by a subject by a non-therapeutic method.

According to another aspect of the present invention, there is provided a method of improving a higher brain dysfunction, a method of improving a mental disorder, or a method of improving a mood disorder in a subject, the method including administering a lactic acid bacterium belonging to the genus *Lactobacillus* to the subject.

Examples

The present invention will be specifically described with reference to the following examples, but the present invention is not limited to these examples. It is noted that units and measurement methods used in the present Examples are in accordance with JIS (Japanese Industrial Standards) unless otherwise defined.

Example 1: Confirmation of Inflammation-Suppressing Effect of Composition Containing *Lactobacillus* Lactic Acid Bacterium (1) Preparation of Composition A lactic acid bacteria starter composed of *Lactobacillus delbrueckii* subsp. *burgaricus* and *Streptococcus thermophilus* was added to a raw material milk (a mixture containing raw milk, skimmed milk powder, cream, sugar, and stevia), and the resulting mixture was maintained at 43° C. for from 4 to 6 hours to ferment the raw material milk, to prepare a yogurt. The heat-treated lactic acid *Lactobacillus plantarum* OLL2712 strain (accession number: FERM BP-11262) was added to the prepared yogurt to prepare the composition (test composition) of the present invention. The heat treatment of the lactic acid bacterium *Lactobacillus plantarum* strain OLL2712 was carried out by concentrating the bacterial cells and then heating the bacterial cells at 60° C. for 10 minutes. The amount of bacterial cells of the lactic acid bacterium contained in the test composition was $5\times10^9$ or more cells/112 g. On the other hand, the same yogurt used in the test composition (yogurt without containing heat-treated lactic acid *Lactobacillus plantarum* OLL2712 strain) was used as the control composition.

(2) Administration of Composition to KK-Ay Mice

Eighteen 5-week-old male KK-Ay mice (manufactured by CLEA Japan, Inc.) were acclimatized for one week and divided into first to third groups (6 mice in each group) based on the body weight, fasting blood glucose level, and blood triglyceride level. At this time, the mice were divided such that there was no significant bias in the mean±standard deviation of the body weight, fasting blood sugar level, and blood triglyceride level of the mice in each group. Mice in each group were reared separately in individual cages. Distilled water, a control composition, and a test composition were orally administered daily to the first, second, and third groups, respectively, for three weeks at a daily dose of 0.5 mL/g body weight.

(3) Measurement of Amount of Inflammatory Cytokines in Brain Tissue

After 3 weeks of oral administration of (2) above, the hippocampus was excised from all mice in each group. The excised hippocampus was homogenized with beads in RIPA buffer (manufactured by Sigma-Aldrich Co. LLC) containing 1% of a protease inhibitor cocktail (manufactured by Sigma-Aldrich Co. LLC) and 1% of a phosphatase inhibitor cocktail (manufactured by Sigma-Aldrich Co. LLC). The homogenate was centrifuged at 14,000×g for 20 minutes at 4° C. and the supernatant was stored at −80° C. The amounts of various inflammatory cytokines were measured using Bio-Plex Pro (trademark) Mouse Cytokine GI23-Plex (manufactured by Bio-Rad Laboratories, Inc.). The obtained measured values were divided by the total protein concentration in the homogenate solution quantitatively determined by the BCA method to calculate the content per unit protein mass.

Table 1 below shows the amounts of various inflammatory cytokines in the hippocampus isolated from mice in each group. As for IL-12, the amounts of IL-12 (p40) consisting of a homodimer of subunit p40 and IL-12 (p70) consisting of subunit p40 and subunit p35 are shown. In Table 1, the unit for the amounts of various inflammatory cytokines is in pg/mg.

TABLE 1

| | 1st group (group treated with distilled water) | 2nd group (group treated with the control composition) | 3rd group (group treated with the test composition) | |
|---|---|---|---|---|
| IL-1a | 6.67 ± 2.82 | 5.60 ± 2.50 | 4.34 ± 1.29 | # |
| IL-1b | 11.38 ± 5.77 | 9.13 ± 3.72 | 7.15 ± 1.96 | |
| IL-6 | 1.16 ± 0.36 | 1.01 ± 0.33 | 0.84 ± 0.18 | # |
| IL-9 | 2.52 ± 0.83 | 1.66 ± 1.84 | 1.31 ± 0.90 | * |
| IL-12(p40) | 4.96 ± 0.95 | 4.29 ± 1.08 | 3.95 ± 0.39 | * |
| IL-12(p70) | 23.09 ± 6.13 | 20.32 ± 5.32 | 17.56 ± 0.94 | # |
| IL-17 | 12.63 ± 2.10 | 11.08 ± 2.05 | 10.22 ± 0.47 | * |
| G-CSF | 1.36 ± 0.43 | 0.95 ± 0.43 | 0.93 ± 0.24 | # |
| GM-CSF | 11.23 ± 3.16 | 9.54 ± 2.54 | 7.40 ± 0.72 | * |
| IFN-g | 12.06 ± 2.76 | 10.64 ± 3.13 | 9.12 ± 0.92 | * |
| MCP-1 | 20.67 ± 5.64 | 17.13 ± 5.06 | 15.20 ± 3.21 | # |
| MIP-1a | 0.77 ± 0.16 | 0.66 ± 0.17 | 0.57 ± 0.06 | * |
| MIP-1b | 30.33 ± 5.50 | 25.34 ± 5.69 | 23.40 ± 1.64 | * |
| TNF-a | 36.29 ± 4.90 | 31.81 ± 6.57 | 31.15 ± 3.14 | # |

Mean ± standard deviation [pg/mg]
#: P < 0.1,
*: P < 0.05,
**: P < 0.01 (both vs. first group) t-test The results in Table 1 show that no significant changes in the amounts of various inflammatory cytokines in the hippocampus were observed in the second group administered with the control composition, compared with the first group. Meanwhile, in the third group administered with the test composition, compared with the first group, the amounts of IL-1, IL-6, IL-9, IL-12, IL-17, G-CSF, GM-CSF, IFN-γ, MCP-1, MIP-1, and TNF-α in the hippocampus significantly decreased ($p<0.05$) or showed a tendency to decrease ($p<0.1$). These results indicate that the composition of the present invention significantly reduces the amounts of various inflammatory cytokines in the hippocampus.

The above-described results indicate that a composition containing a lactic acid bacterium belonging to the genus *Lactobacillus* can effectively suppress brain tissue inflammation, especially hippocampal inflammation. In addition, conventionally, it has been suggested that inflammation in brain tissue, especially inflammation in the hippocampus, is involved in the development/progression of brain diseases such as Alzheimer's disease. Therefore, the above-described results indicate that a composition containing a lactic acid bacterium belonging to the genus *Lactobacillus* can treat and/or prevent various brain diseases that develop/progress caused by inflammation in brain tissue. Further, it has been suggested that inflammatory cytokines damage nerve cells in brain tissue and inhibit the formation of normal nerve cells, causing a mental disorder or a mood disorder. Therefore, the above-described results indicate that a composition containing a lactic acid bacterium belonging to the genus *Lactobacillus* can reduce the amounts of inflammatory cytokines in brain tissue and treat and/or prevent a mental disorder or a mood disorder. In other words, the above-described results indicate that the composition of the present invention can effectively suppress brain tissue inflammation, especially hippocampal inflammation. Moreover, the above-described results indicate that the composition can be used to improve disorders and diseases caused by brain tissue inflammation, particularly disorders and diseases caused by hippocampal inflammation, such as deterioration of higher brain functions, mental disorders, and mood disorders.

INDUSTRIAL APPLICABILITY

According to the present invention, the amounts of inflammatory cytokines in the brain tissue of a subject can be effectively reduced, and inflammation in the brain tissue of a subject can be suppressed. Moreover, according to the present invention, disorders and diseases caused by inflammation in brain tissue can be improved by suppressing inflammation in the brain tissue of a subject.

The invention claimed is:

1. A method of suppressing inflammation in a brain tissue of a subject, comprising allowing the subject to ingest an effective amount of a lactic acid bacterium belonging to *Lactobacillus plantarum*, wherein the lactic acid bacterium has a 16S rRNA gene having a similarity of 99% or more to the nucleotide sequence represented by SEQ ID NO: 1.

2. A method of improving a disorder caused by inflammation of a brain tissue of a subject, comprising allowing the subject to ingest an effective amount of a lactic acid bacterium belonging to *Lactobacillus plantarum*, wherein the lactic acid bacterium has a 16S rRNA gene having a similarity of 99% or more to the nucleotide sequence represented by SEQ ID NO: 1.

3. A method of improving a disease caused by the higher brain dysfunction in a subject, comprising allowing the subject to ingest an effective amount of a lactic acid bacterium belonging to *Lactobacillus plantarum*, wherein the lactic acid bacterium has a 16S rRNA gene having a similarity of 99% or more to the nucleotide sequence represented by SEQ ID NO: 1.

4. A method of improving at least one disorder selected from the group consisting of a mental disorder, a mood disorder, and a higher brain dysfunction in a subject, comprising allowing the subject to ingest an effective amount of a lactic acid bacterium belonging to *Lactobacillus plantarum*, wherein the lactic acid bacterium has a 16S rRNA gene having a similarity of 99% or more to the nucleotide sequence represented by SEQ ID NO: 1.

5. The method according to claim 1, wherein the subject is human.

6. The method according to claim 1, wherein the brain tissue is hippocampus.

7. The method according to claim 2, wherein the disorder is at least one disorder selected from the group consisting of a mental disorder, a mood disorder and a higher brain dysfunction.

8. The method according to claim 4, wherein the higher brain dysfunction is a disorder of at least one function selected from the group consisting of selective attention function, cognitive function, memory function, executive function, and learning function.

9. The method according to claim 3, wherein the disease is selected from the group consisting of Alzheimer's dementia, dementia with Lewy bodies, frontotemporal dementia, amnestic syndrome, generalized attention disorder, social behavior disorder, and memory disorder.

10. The method according to claim 1, wherein the lactic acid bacterium has an activity of reducing an amount of at least one inflammatory cytokine selected from the group consisting of interleukin-1, interleukin-6, interleukin-9, interleukin-12, interleukin-17, a granulocyte colony-stimulating factor, a granulocyte monocyte-colony stimulating factor, interferon-γ, monocyte chemoattractant protein-1, macrophage inflammatory protein-1, and a tumor necrosis factor in the brain tissue.

11. The method according to claim 1, wherein the lactic acid bacterium is *Lactobacillus plantarum* OLL2712 strain deposited under accession number FERM BP-11262.

12. The method according to claim 1, wherein the lactic acid bacterium contains a dead bacterial cell of the lactic acid bacterium.

13. The method according to claim 1, wherein the lactic acid bacterium contains a heat-treated dead bacterial cell.

14. The method according to claim 2, wherein the lactic acid bacterium is *Lactobacillus plantarum* OLL2712 strain deposited under accession number FERM BP-11262.

15. The method according to claim 3, wherein the lactic acid bacterium is *Lactobacillus plantarum* OLL2712 strain deposited under accession number FERM BP-11262.

16. The method according to claim 4, wherein the lactic acid bacterium is *Lactobacillus plantarum* OLL2712 strain deposited under accession number FERM BP-11262.

* * * * *

SEQUENCE LISTING

<160> NUMBER OF SEQ ID NOS: 1

<210> SEQ ID NO 1
<211> LENGTH: 533
<212> TYPE: DNA
<213> ORGANISM: Lactobacillus plantarum

<400> SEQUENCE: 1
ttaaagctgg cggcgtgcct aatacatgca agtcgaacga actctggtat tgattggtgc 60
ttgcatcatg atttacattt gagtgagtgg cgaactggtg agtaacacgt gggaaacctg 120
cccagaagcg ggggataaca cctggaaaca gatgctaata ccgcataaca acttggaccg 180
catggtccga gtttgaaaga tggcttcggc tatcactttt ggatggtccc gcggcgtatt 240
agctagatgg tggggtaacg gctcaccatg gcaatgatac gtagccgacc tgagagggta 300
atcggccaca ttgggactga gacacggccc aaactcctac gggaggcagc agtagggaat 360
cttccacaat ggacgaaagt ctgatggagc aacgccgcgt gagtgaagaa gggtttcggc 420
tcgtaaaact ctgttgttaa agaagaacat atctgagagt aactgttcag gtattgacgg 480
tatttaacca gaaagccacg gctaactacg tgccagcagc ccgcgggtct cta 533